US011071615B2

(12) United States Patent
Austin

(10) Patent No.: US 11,071,615 B2
(45) Date of Patent: Jul. 27, 2021

(54) BIRTHING SENSOR

(71) Applicant: MOOCALL LTD, Fashion (IE)

(72) Inventor: Niall Austin, Birr (IE)

(73) Assignee: MOOCALL LTD, Dublin (IE)

( * ) Notice: Subject to any disclaimer, the term of this patent is extended or adjusted under 35 U.S.C. 154(b) by 774 days.

(21) Appl. No.: 15/314,879

(22) PCT Filed: May 29, 2015

(86) PCT No.: PCT/EP2015/062043
§ 371 (c)(1),
(2) Date: Nov. 29, 2016

(87) PCT Pub. No.: WO2015/181385
PCT Pub. Date: Dec. 3, 2015

(65) Prior Publication Data

US 2017/0196668 A1 Jul. 13, 2017

(30) Foreign Application Priority Data

May 30, 2014 (GB) ..................................... 1409612

(51) Int. Cl.
*A61B 5/00* (2006.01)
*A61D 17/00* (2006.01)

(52) U.S. Cl.
CPC .................................. *A61D 17/008* (2013.01)

(58) Field of Classification Search
CPC .................................................... A61D 17/008
See application file for complete search history.

(56) References Cited

U.S. PATENT DOCUMENTS 5,655,026 A * 8/1997 Peters .................. H04R 1/1066 381/370
5,881,673 A * 3/1999 Beach .................. A61D 17/002 119/174

(Continued)

FOREIGN PATENT DOCUMENTS

CH 683337 A5 * 2/1994 ........... B65D 81/133
FR 2618051 A1 1/1989

(Continued)

OTHER PUBLICATIONS

The English-language machine translation of CH 683337 A5 is attached herewith (Year: 2019).*

(Continued)

*Primary Examiner* — Navin Natnithithadha
*Assistant Examiner* — Andrey Shostak
(74) *Attorney, Agent, or Firm* — Brian J. Colandreo; Michael T. Abramson; Holland & Knight LLP

(57) ABSTRACT

This invention relates to a birthing sensor (1) for mounting on the tail of a pregnant animal. The birthing sensor comprises a casing (3) and an adjustable strap (5) for securing the casing to the tail of the pregnant animal. The casing houses monitoring equipment, communication equipment and a power supply. There is provided a padding insert (7, 37, 47) for location between the casing, the strap and the animal's tail. The padding insert comprises a sheet of resiliently deformable material, such as rubber, having a plurality of ventilation passageways formed therein. The ventilation passageways allow passage of air over the cow's tail underneath the sensor and further allow escape of urine and faeces from under the sensor. The passageways may be formed by having a plurality of upstanding bosses (9) on the surface of the padding insert and the passageways are the spaces between these upstanding bosses (9).

19 Claims, 12 Drawing Sheets

(56) References Cited

U.S. PATENT DOCUMENTS

| | | | | |
|---|---|---|---|---|
| 6,432,006 | B1 * | 8/2002 | Tribble | A63B 60/10 473/564 |
| 8,652,164 | B1 * | 2/2014 | Aston | A61B 17/1327 606/203 |
| 9,119,379 | B1 * | 9/2015 | Yancey | A61B 5/0004 |
| 2002/0168881 | A1 * | 11/2002 | Hwang | F21S 8/035 439/11 |
| 2006/0079964 | A1 * | 4/2006 | Perkins | A61F 2/78 623/36 |
| 2010/0036277 | A1 * | 2/2010 | Austin | A61D 13/00 600/549 |
| 2011/0306903 | A1 * | 12/2011 | Crabtree | A61B 5/103 600/595 |
| 2012/0289858 | A1 * | 11/2012 | Ouyang | A61B 10/0275 600/562 |
| 2013/0328574 | A1 * | 12/2013 | Chiou | A61B 5/6892 324/649 |
| 2014/0275891 | A1 * | 9/2014 | Muehlemann | A61B 5/6801 600/328 |
| 2014/0276389 | A1 * | 9/2014 | Walker | A61M 25/09041 604/95.01 |
| 2015/0151064 | A1 * | 6/2015 | Hieber | A61M 16/0683 128/206.24 |
| 2015/0257471 | A1 * | 9/2015 | Warmouth | A42B 3/122 2/413 |

FOREIGN PATENT DOCUMENTS

| | | | | |
|---|---|---|---|---|
| GB | 2247955 | A1 | 3/1992 | |
| WO | 0060979 | A1 | 10/2000 | |
| WO | WO-0203881 | A1 * | 1/2002 | G01K 13/002 |
| WO | 2013186232 | A1 | 12/2013 | |
| WO | 2015181385 | A1 | 12/2015 | |

OTHER PUBLICATIONS

English-language machine translation of WO 02/03881 (Year: 2002).*

International Search Report issued in PCT Application Serial No. PCT/EP2015/062043 dated Dec. 3, 2015.

* cited by examiner

BIRTHING SENSOR

CROSS-REFERENCE TO RELATED APPLICATIONS

This application is a U.S. National Stage of International Patent Application No. PCT/EP2015/062043, filed 29 May 2015, which claims priority to Great Britain Patent Application No: 1409612.7, filed on 30 May 2014, the disclosure of which is incorporated herein by reference in its entirety.

TECHNICAL FIELD

This invention relates to a birthing sensor.

BACKGROUND ART

Birthing sensors are commonly placed on cows and other pregnant animals in the days leading up to the animal giving birth. The birthing sensors are used to provide an early warning system for the farmer that the animal is going into labour and allows the farmer to attend the birth and assist in the delivery of the newborn animal. In this way, the number of successful deliveries is increased.

There are numerous different types of birthing sensors. These include temperature probe sensors that must be placed internal the animal, heart monitor sensors that are placed on a strap around the crops of the animal and movement sensors placed on the tail of the animal. There are however several problems with the known birthing sensors.

First of all, those birthing sensors that are inserted into the animal often require the assistance of a vet in order to position the sensors correctly which is prohibitively expensive for most farmers. Secondly, the placement of these internal sensors can cause discomfort and distress to the animal which is highly undesirable. Thirdly, the other types of known birthing sensors that are placed externally are often difficult to mount correctly onto an animal and it is not uncommon for the external sensors to become dislodged, rendering them ineffective, or damaged through movement of the animal. Fourth, it is not uncommon for these external sensors to cause injury to the animal wearing the sensor or to another animal in close proximity to that animal. Fifth, many of the known external sensors are cumbersome and require several minutes to position the sensors on the animal. This is highly undesirable as the longer it takes to place the sensor on the animal, the more likely it is that the animal will become restless during the procedure and move. This movement can result in the sensor being incorrectly positioned on the animal or indeed the movement can result in injury to the person placing the sensor on the animal. Sixth, it is not uncommon for the birthing sensors to move over the course of a few days, rendering them inaccurate. Seventh, it is not uncommon for the birthing sensors to cause irritation to the animal if they are left on the animal for extended periods of time. This irritation can lead to sores and infection.

This is a significant problem for the known birthing sensors as the infection can be potentially life threatening to the animal and their unborn. Often, the sensor will have to be removed from the animal before the birth to ensure that infection does not arise and this defeats the purpose of having the sensor in the first place.

Various solutions to the problems with the known birthing sensors have been proposed. Indeed, reference is made to the Applicant's own co-pending PCT patent application no. PCT/EP2013/062066 entitled "A birthing sensor", the entire disclosure of which is incorporated herein by way of reference. This PCT application describes a birthing sensor that can be placed quickly onto the tail of an animal. In light of the fact that the birthing sensor can be placed quickly onto the tail of an animal, the birthing sensor described will reduce the likelihood or injury to the person placing the birthing sensor onto the animal and will increase the likelihood of the sensor being placed correctly on the animal.

The present invention is directed towards providing a birthing sensor that overcomes at least some of the problems of the known birthing sensors. It is a further object of the present invention to provide a birthing sensor that is an improvement over the solution described in PCT/EP2013/062066. It is a further object of the present invention to provide a useful alternative choice to the consumer.

SUMMARY OF INVENTION

According to the invention there is provided a birthing sensor for mounting on the tail of a pregnant animal comprising a casing and an adjustable strap for securing the casing to the tail of a pregnant animal, the casing housing monitoring equipment, communication equipment and a power supply therein, characterised in that there is provided a padding insert mounted on the casing and the strap for location intermediate the casing, the strap and the animal's tail, the padding insert comprising a resiliently deformable material having a plurality of ventilation passageways formed therein for throughpassage of air when the birthing sensor is mounted on the tail of a pregnant animal.

By having such a birthing sensor having a padding insert with ventilation passageways formed therein, the birthing sensor can be left on the animal for prolonged periods of time without causing irritation or infection to the animal. This is important as the birthing sensor will not have to be taken off prematurely and the animal will be comfortable and will not be distressed as a result of the sensor placement. By having ventilation passageways, air can circulate around the animal's tail under the sensor and other materials such as faeces and urine will be able to escape from underneath the sensor reducing the likelihood of infection to the animal. Furthermore, it has been found that by providing a padding insert of resiliently deformable material with ventilation passageways, the birthing sensor will be less inclined to slip down or around the animal's tail which would render the birthing sensor useless and instead, the birthing sensor has been found to maintain its position on the tail far better over prolonged periods of time.

In one embodiment of the invention there is provided a birthing sensor in which the padding insert comprises a sheet of resiliently deformable material having a plurality of upstanding bosses formed on one surface thereof. This is seen as a particularly preferred embodiment of the present invention that is seen as a simple way of providing ventilation passageways in the padding insert while at the same time improving the grip of the sensor on the animal's tail.

In one embodiment of the invention there is provided a birthing sensor in which the plurality of upstanding bosses are frustoconical in shape.

In one embodiment of the invention there is provided a birthing sensor in which the plurality of upstanding bosses are substantially hollow. By having substantially hollow upstanding bosses, the bosses can compress and will be more comfortable for the cow. Furthermore, the hollow bosses can receive an insert which will allow adjustment of the birthing sensor to accommodate a variety of sizes of animal's tails.

In one embodiment of the invention there is provided a birthing sensor in which there is provided a second separate sheet of resiliently deformable material having a plurality of upstanding bosses formed on one surface thereof for placement overlapping the first sheet of resiliently deformable material. The second separate sheet of resiliently deformable material will allow adjustment of the birthing sensor to accommodate a variety of sizes of animal's tails. If the second separate sheet of resiliently deformable material is placed on top of or underneath the first sheet of resiliently deformable material before the sensor is placed on an animal's tail, the birthing sensor can be used on tails of smaller circumference but will still be held securely in position on the tail.

In one embodiment of the invention there is provided a birthing sensor in which the plurality of upstanding bosses are formed on the second separate sheet of resiliently deformable material are conical in shape.

In one embodiment of the invention there is provided a birthing sensor in which the padding insert is releasably secured to at least one of the casing and the strap. By having the padding insert releasably secured in position, other padding inserts can be placed underneath the padding insert and furthermore the padding inserts can be replaced and interchanged.

In one embodiment of the invention there is provided a birthing sensor in which the casing is provided with at least one locating spigot and the padding insert is provided with at least one complementary spigot-receiving cutout. This is seen as a simple way of positioning the padding insert onto the animal's tail.

In one embodiment of the invention there is provided a birthing sensor in which the padding insert is substantially T-shaped with the cross portion of the T-shaped body aligned along the casing and the upright portion of the T-shaped body aligned along the adjustable strap.

In one embodiment of the invention there is provided a birthing sensor in which the adjustable strap comprises a ratchet strap system including a toothed strap connected to the casing at one of its ends and a buckle mounted on the casing for releasably engaging the toothed strap intermediate its ends, the buckle being arranged so that as the buckle closes, the buckle tightens the strap by engaging one or more of the teeth on the strap and pulling the strap tighter.

This is seen as a particularly preferred embodiment of the present invention. The ratchet strap system will enable the birthing sensor to be placed onto the animal in a matter of seconds in a very convenient manner. In order to place the birthing sensor onto an animal, the operator will simply place the sensor against the tail with one hand and using the other hand will lead the toothed strap around the cow's tail and through the buckle. As the toothed strap is led through the buckle, it will immediately start to provide an engagement between the strap and the buckle facilitating the placement of the sensor onto the cow's tail. Once the strap is relatively secure, the buckle can be closed and as the buckle is closed, it will perform the last tightening of the strap to ensure that the sensor is held in position.

In one embodiment of the invention there is provided a birthing sensor in which the buckle is inset into the casing. By having the buckle inset into the casing, this will obviate the possibility of the buckle becoming inadvertently dislodged and furthermore will obviate the possibility of the buckle injuring another animal.

In one embodiment of the invention there is provided a birthing sensor in which there is provided a removable protective cap mounted on the casing above the buckle. The removable protective cap will further ensure that the buckle is not inadvertently opened.

In one embodiment of the invention there is provided a birthing sensor in which the adjustable strap is a two part strap including a first part formed integrally with the casing and extending outwardly therefrom and a second part connected to the first part, the second part being narrower than the first part and suitable for engagement in a buckle.

In one embodiment of the invention there is provided a birthing sensor in which the casing is turtle-shell shaped with a curved outer surface that tapers inwardly at each end. This is seen as a particularly suitable configuration of casing that is a significant improvement over the existing offerings. The turtle-shell shaped casing will allow the loads from any impact suffered by the casing to be spread evenly about the casing reducing the possibility of damage to the casing. Furthermore, the casing will be less likely to catch on gates and the like which could cause the birthing sensor to move about the tail or to become dislodged. Finally, the birthing sensor so-shaped will be less likely to cause injury to the animal wearing the sensor or to other animals in the vicinity.

In one embodiment of the invention there is provided a birthing sensor in which the power supply comprises a rechargeable battery and there is provided a battery charging port located at the end of the casing that in use is directed towards the ground and in which there is provided a removable gasket mounted over the battery charging port.

In one embodiment of the invention there is provided a birthing sensor in which the casing is constructed from a flexible plastic material.

In one embodiment of the invention there is provided a birthing sensor in which the casing is constructed from polypropylene.

In one embodiment of the invention there is provided a birthing sensor in which the padding insert is constructed from rubber silicone.

In one embodiment of the invention there is provided a birthing sensor in which the padding insert is constructed from latex rubber.

BRIEF DESCRIPTION OF THE DRAWINGS

The invention will now be more clearly understood from the following description of some embodiments thereof given by way of example only with reference to the accompanying drawings, in which.

DETAILED DESCRIPTION OF THE DRAWINGS

Figure 1:
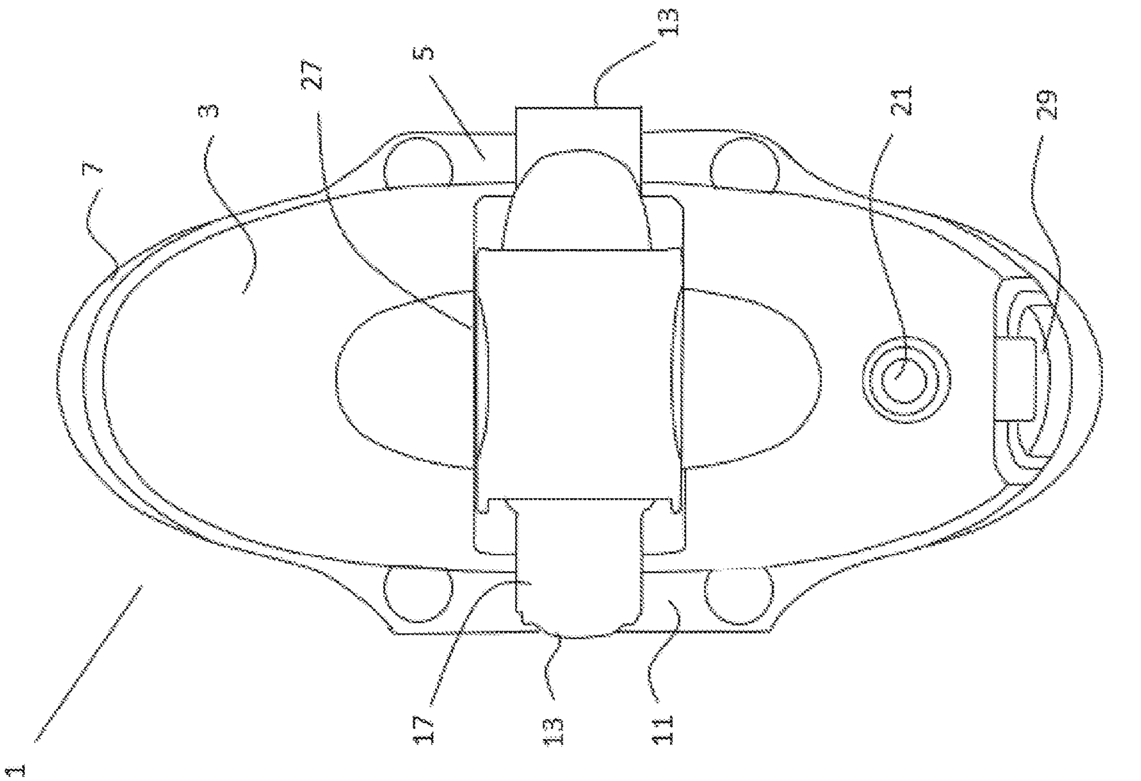
FIG. 1 is a front view of a birthing sensor according to the invention.
Figure 2:
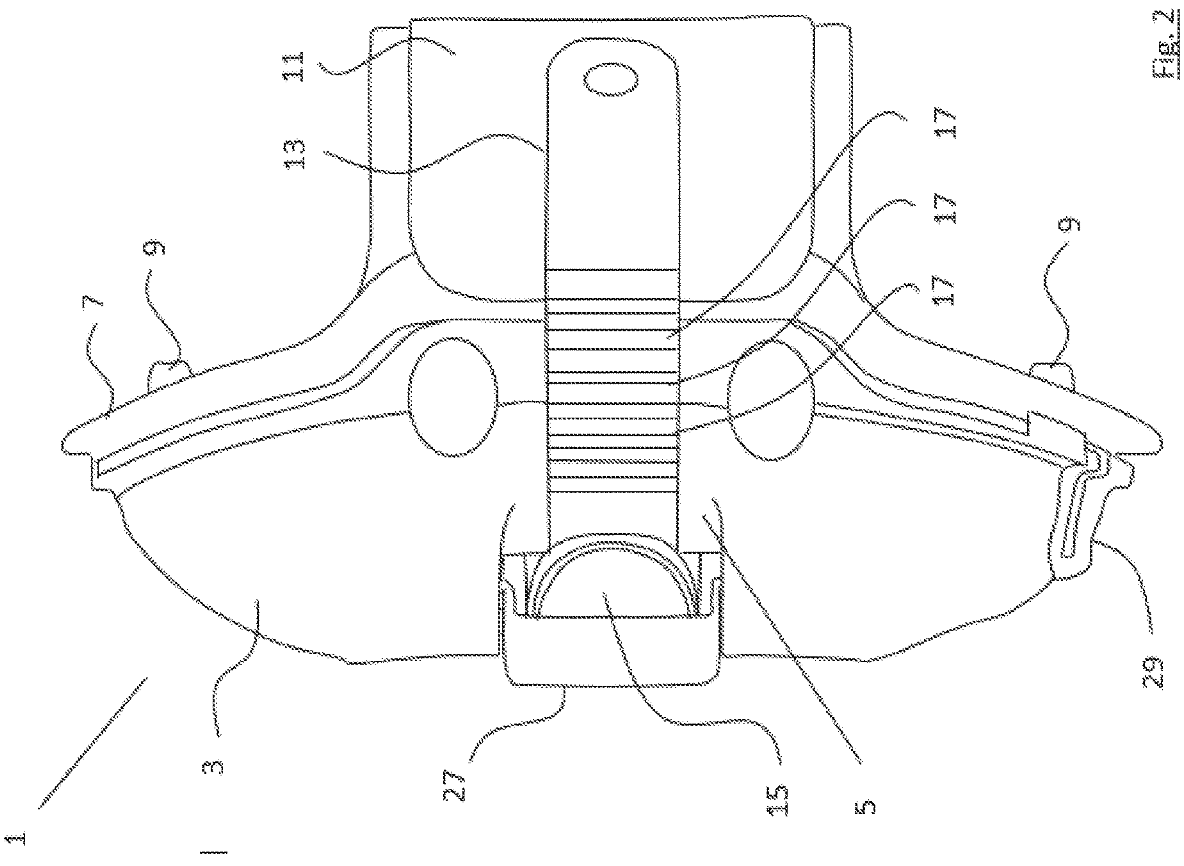
FIG. 2 is a side view of the birthing sensor according to the invention.
Figure 3:
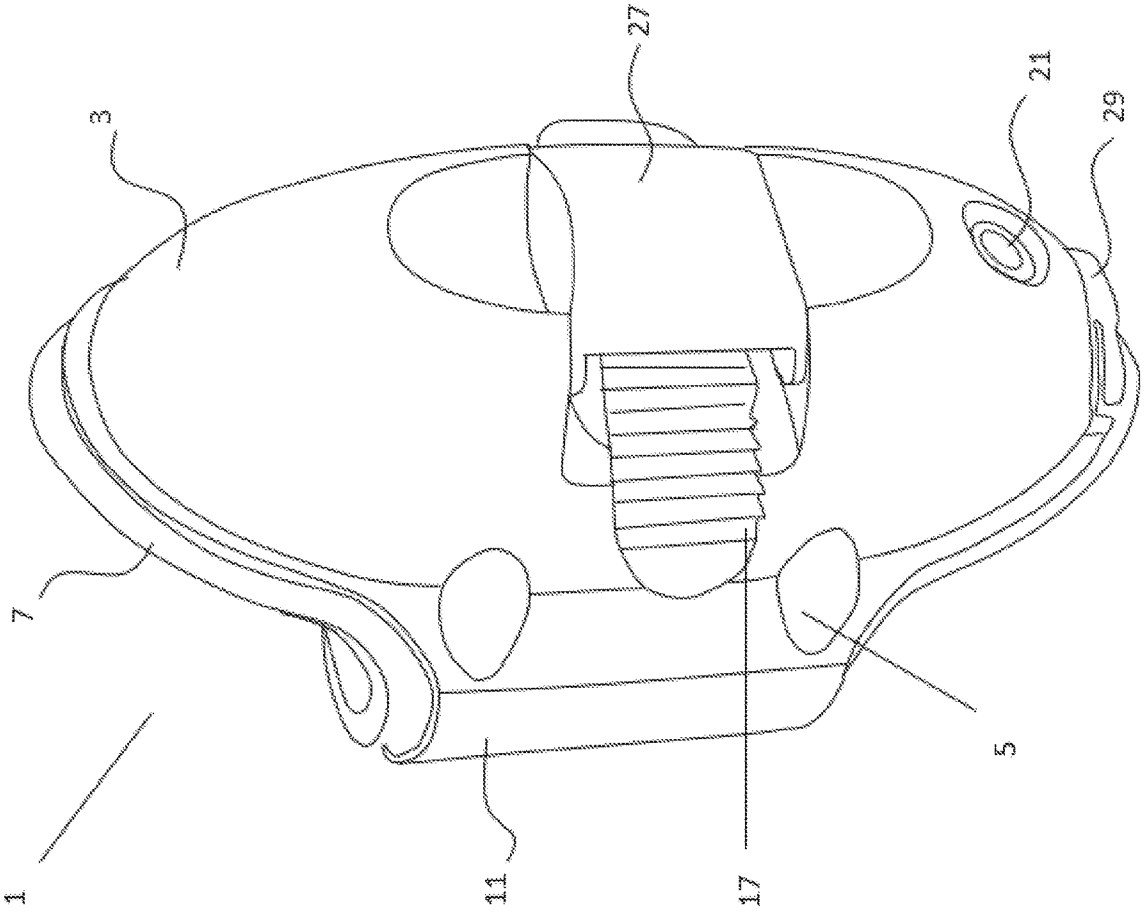
FIG. 3 is a front perspective view of the birthing sensor.
Figure 4:
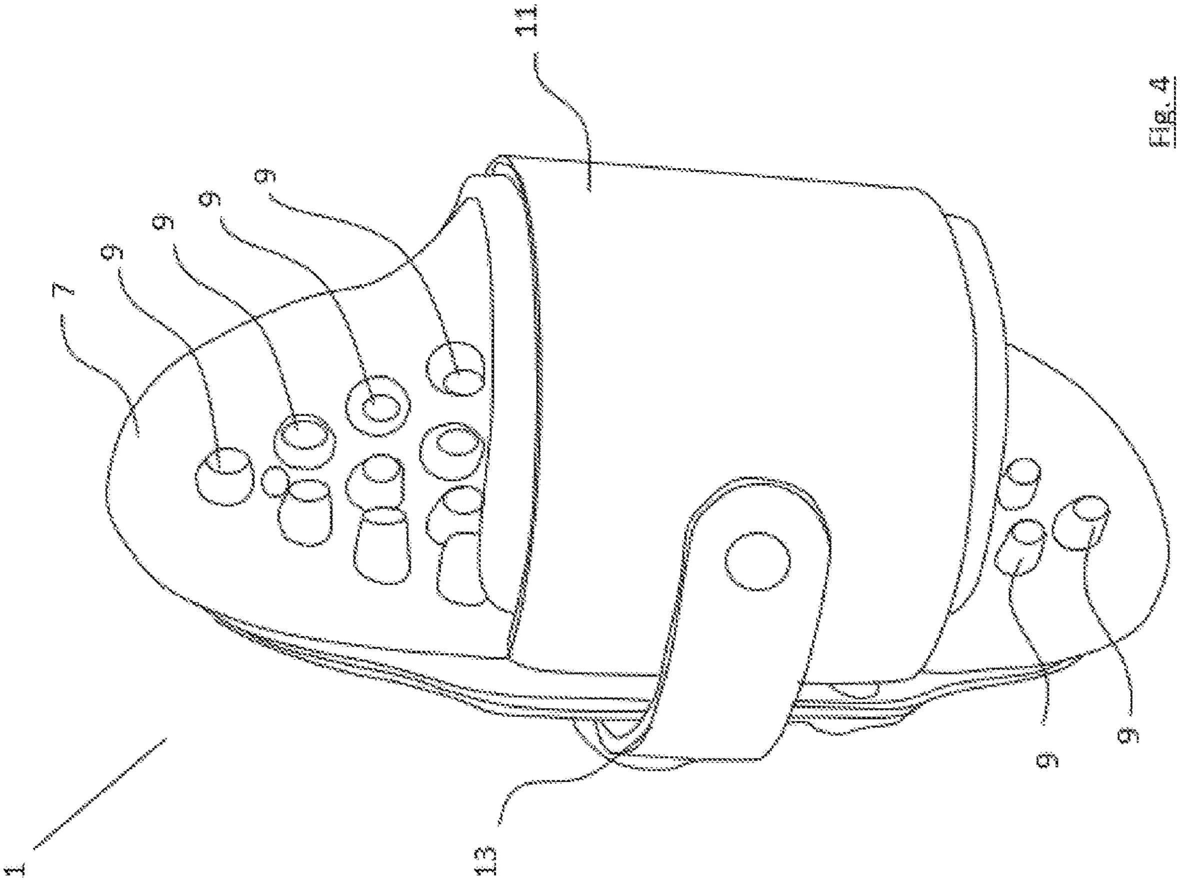
FIG. 4 is a rear perspective view of the birthing sensor.
Figure 5:
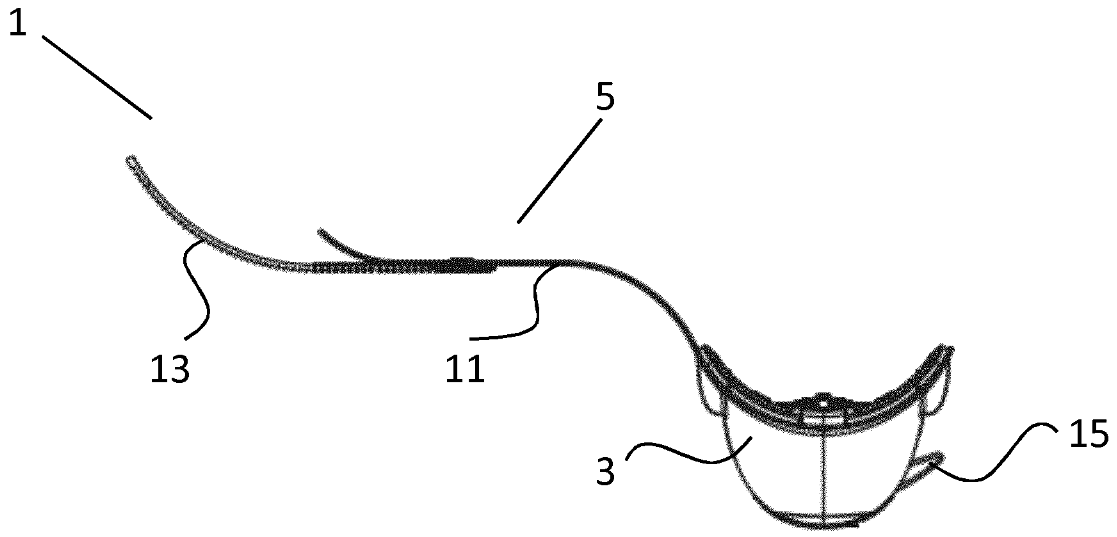
FIG. 5 is a top plan view of the birthing sensor with the strap open.
Figure 6:
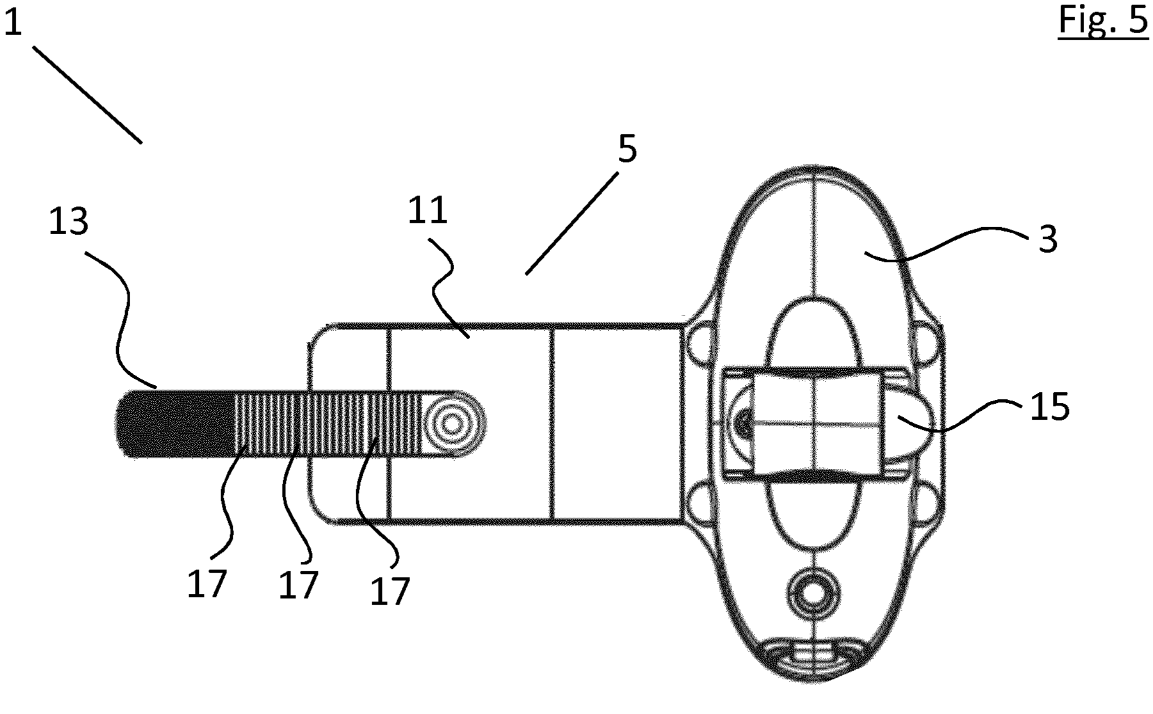
FIG. 6 is a front view of the birthing sensor with the strap open.

Referring to FIGS. 1 to 9, there is shown a birthing sensor, indicated generally by the reference numeral 1, for mounting on the tail of a pregnant animal (not shown), the birthing sensor 1 comprising a casing 3 and a strap 5. The birthing sensor 1 further comprises a padding insert 7 provided by way of a sheet of resiliently deformable material having a plurality of upstanding bosses 9. The upstanding bosses 9 are substantially hollow frustoconically-shaped bosses that provide a secure, non-slip engagement between the tail of the animal and the birthing sensor.

The strap 5 comprises a two part strap including a first part 11 that is formed integrally with the casing 3 and a second, narrower part 13 that extends from the first part 11. The second, narrower part 13 of the strap 5 is connected to the first part 11 of the strap adjacent one of its ends 15 and is dimensioned for insertion into a buckle 15 mounted on the casing. The second part 13 of the strap comprises a toothed strap having a plurality of teeth 17 formed along it length and the buckle 15 and second part of the strap 13 combine to form a ratchet-type securing arrangement in which as the strap 13 is fed through the buckle, the buckle will begin to engage the strap. As the buckle 15 is closed, the buckle will draw the strap 13 tighter around the animal's tail.

Importantly, as the buckle is closed and the birthing sensor is mounted on the animal's tail, a plurality of air passageways are formed in the gaps intermediate the upstanding bosses 9 and this will allow circulation of air around the animal's tail even when the sensor is mounted on the animal's tail. The air passageways will also allow other material such as urine and faeces to pass though the passageways rather than becoming trapped under the strap, thereby avoiding irritation to the animal.

Figure 9:
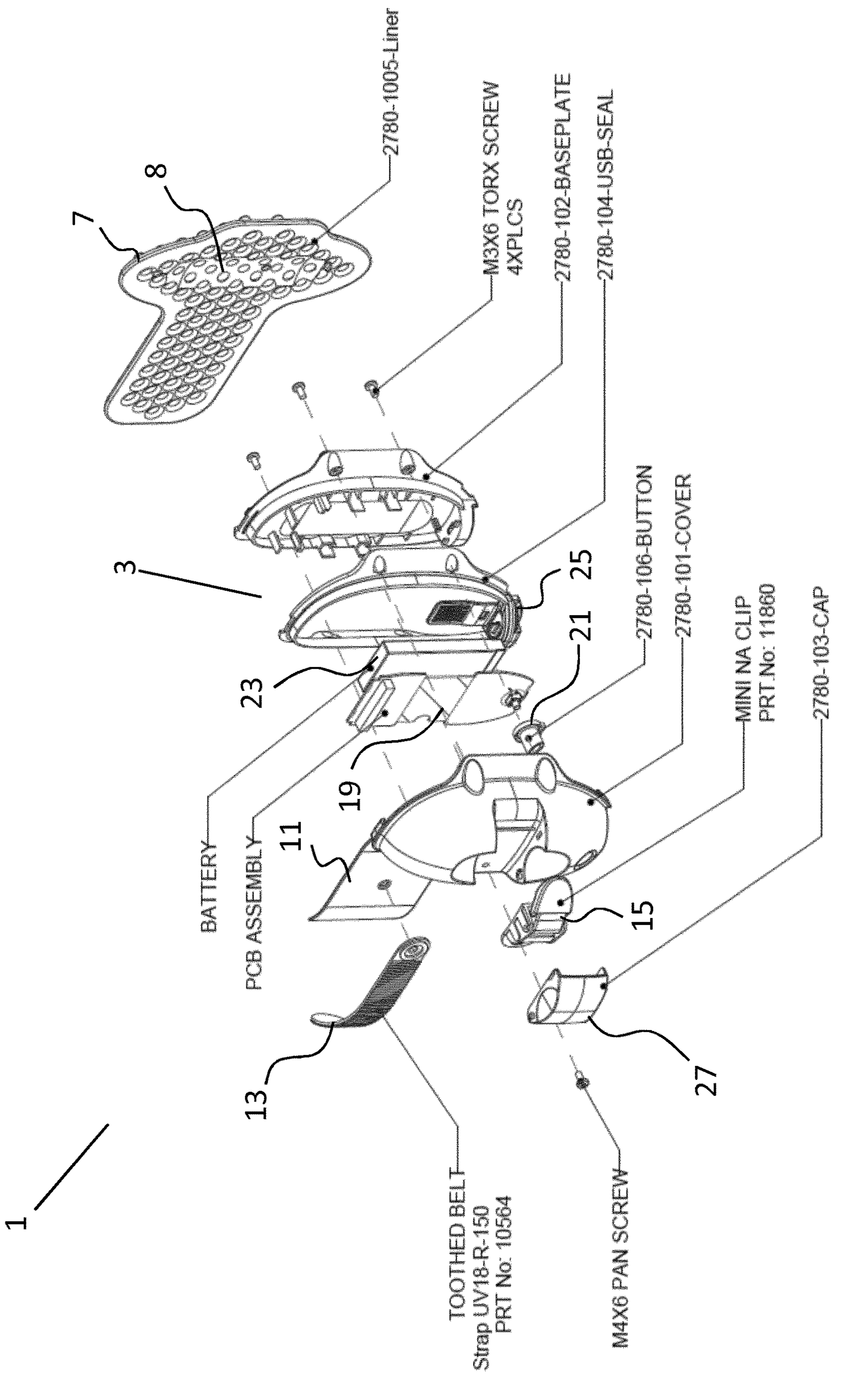
FIG. 9 is an exploded view of the birthing sensor.

Referring specifically to FIG. 9, there is shown an exploded view of the birthing sensor 1, illustrating some of the internal components of the birthing sensor. The birthing sensor has a PCB assembly 19 on which various measurement equipment and communication equipment is provided. The PCB assembly is also provided with a reset button 21 which is accessible from external the casing 3. The birthing sensor is also provided with a rechargeable battery 23 and there is provided a charging port 25 adjacent the base of the casing 3 for recharging the battery.

The measurement equipment mounted on the PCB assembly includes, for example, a three axis accelerometer for detecting the orientation of the sensor and also the movements of the sensor. The communication equipment may comprise a universal SIM for communications over a wireless communications network such as a mobile telephony network, a wireless local area network (WLAN) or a wireless personal area network (WPAN). This will allow the birthing sensor to communicate with one or more of a remote computing device such as a mobile phone, a smart phone, a personal digital assistant (PDA), a tablet, a phablet, a laptop or a personal computer. In this way, the birthing sensor can communicate sensing information to a device operated by the farmer such as a mobile phone and/or another remote computing device. Furthermore, in some embodiments, the birthing sensor can receive communications from a remote computing device. For example, a remote computing device such as a mobile telephone could be used to poll the birthing sensor for a status update which in turn would be returned to the mobile telephone or a remote computing device can be used to provide a software update to the birthing sensor, for example.

Figure 7:
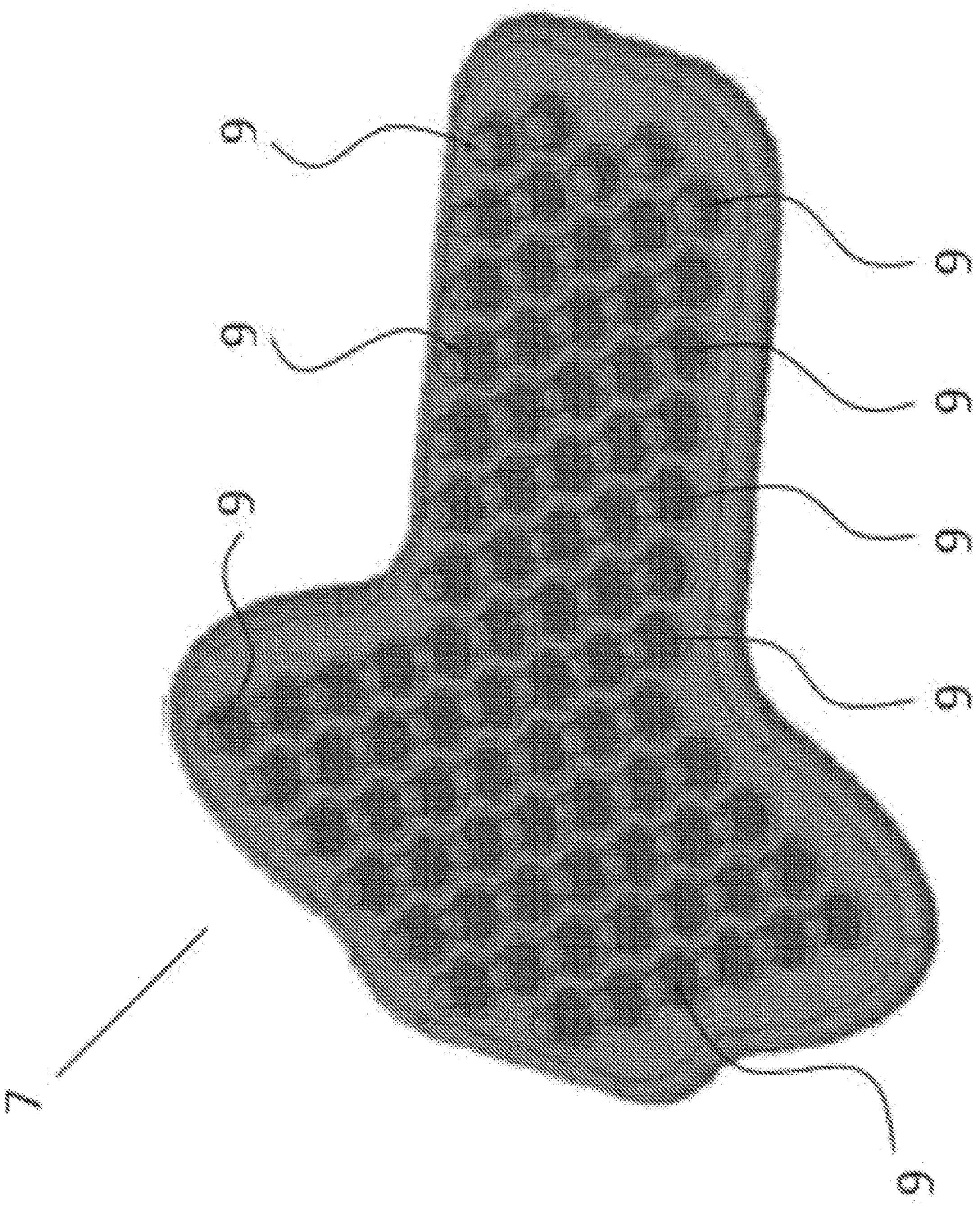
FIG. 7 is a perspective view of a padding insert.
Figure 8:
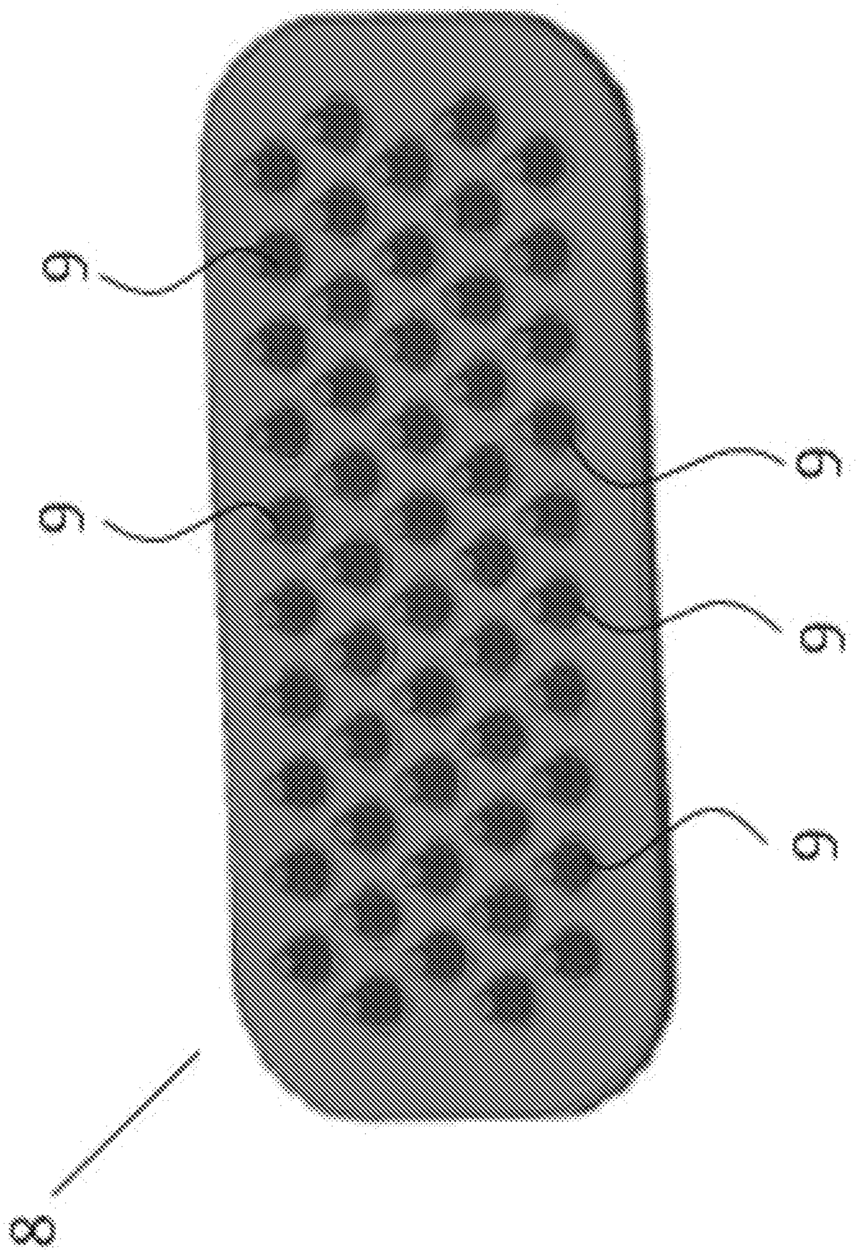
FIG. 8 is a perspective view of a second resiliently deformable sheet for use with the padding insert.

In addition to the foregoing, it can be seen that there is a second resiliently deformable sheet 8 that overlaps with the padding insert 7 to allow adjustment of the padding insert and to allow for animals with a narrower circumference tail to be accommodated. The second resiliently deformable sheet 8 does not have to be T-shaped like the first padding insert 7 and instead it can only overlap a portion of the padding insert 7. The second resiliently deformable sheet 8 may also have similar frustoconically shaped bosses on it's surface or indeed it may have conically shaped bosses thereon. It should be noted that the padding insert 7 and the resiliently deformable sheet 8 illustrated in FIGS. 7 and 8 are not shown to scale and the bosses on the surface of the sheet 8, if provided, will align with the bosses of the padding insert 7.

Referring once again to FIGS. 1 to 8, it can be seen that there are various other advantageous features of the present invention. For example, the buckle 15 is provided with a cap 27. The cap 27 is hingedly mounted on the casing 3 and can pivot out of the way of the buckle or into a position effectively covering the buckle 15. When covering the buckle 15, the cap will prevent inadvertent release of the buckle 15 and the strap 5. Furthermore, the buckle 15 is inset into the casing to avoid the buckle being snagged on a gate or the like or injuring another animal. This will also protect the buckle from inadvertent release and damage. In the embodiment shown, there is provided a rechargeable battery charging port at the base of the casing 3 and a gasket 29 is provided over the port to prevent ingress of dirt and moisture into the casing 3. In addition to the foregoing, there is provided a reset button 21 on the front of the casing which will allow the farmer or other operative to quickly reset the device when placing the device on another animal. This will allow the device to be used on a plurality of different animals in the herd in quick succession.

In the embodiments shown, the device is constructed from a flexible plastic material, in this case polypropylene. Alternatively, the device could be constructed from other flexible plastic material. This will allow the provision of a flexible integral strap portion 11 with the casing 3. The padded insert is constructed from a resiliently deformable material such as rubber. It is envisaged that the padded inserts 7, 8 may be constructed from one of rubber silicone and latex rubber. Alternatively, instead of latex rubber or silicone rubber, other resiliently deformable materials could be used. The rubber padded inserts in the embodiments shown are shore 30.

Figure 10:
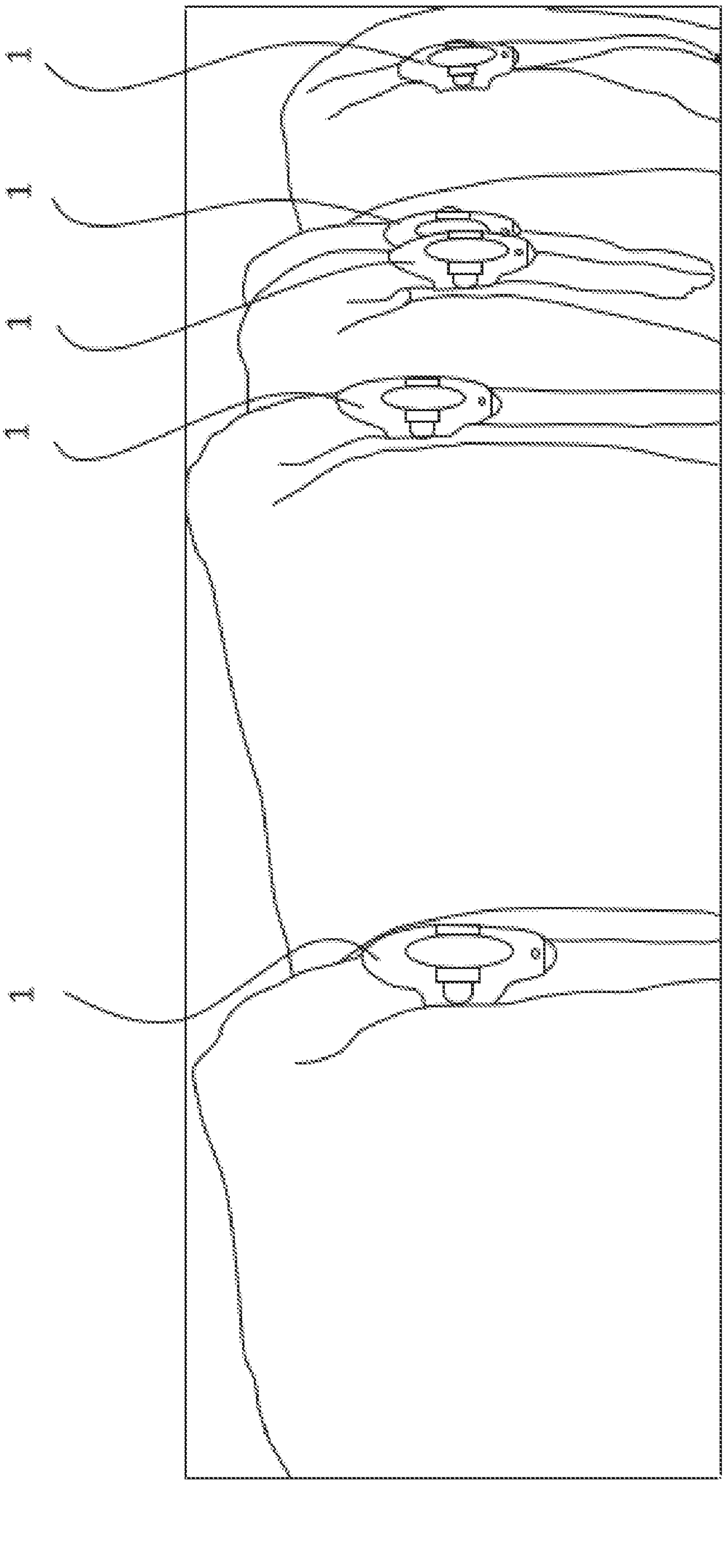
FIG. 10 is a view of the birthing sensor mounted on a cow's tail.

Referring now to FIG. 10, there is shown a plurality of birthing sensors mounted on different cow's tails. A significant advantage of the present invention is that the birthing sensor according to the invention can be placed on a wide variety of cows of different shapes and sizes. This is due in part to the firm connection that is achieved with the padding insert and also to the tolerance and adjustability provided by the padded insert, the auxiliary or second padded insert and the strap.

Figure 11:
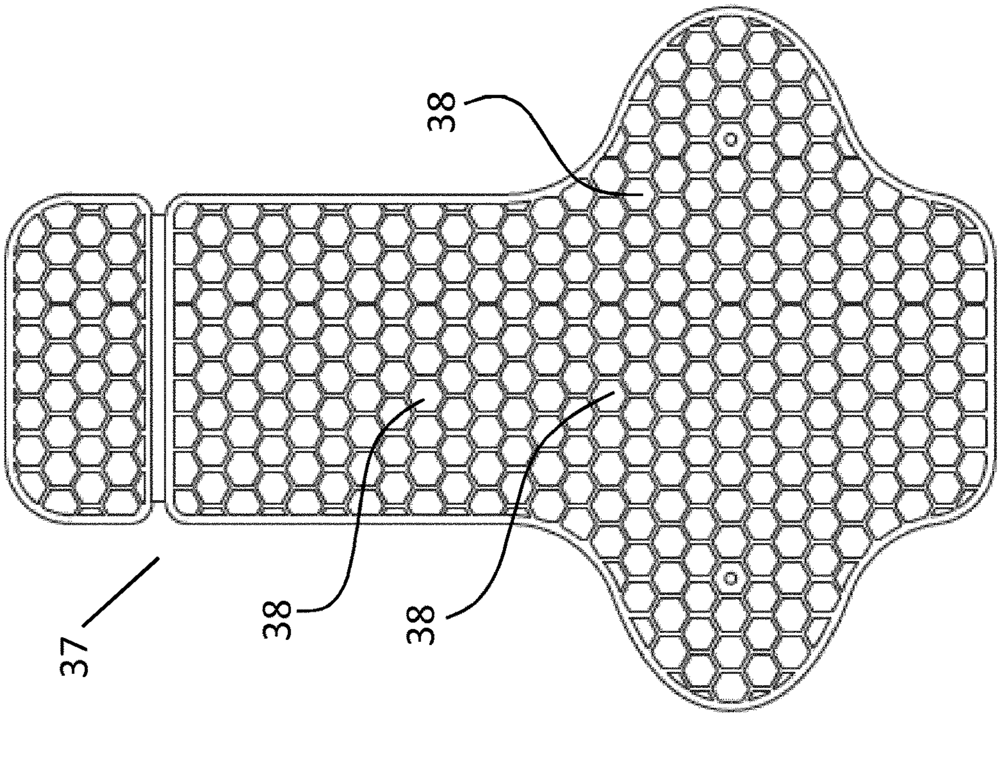
FIG. 11 is front view of an alternative padding insert according to the invention.

Referring now to FIG. 11, there is shown a front view of an alternative embodiment of a padding insert 37 having a honeycomb pattern of hexagonal ventilation apertures 38. The ventilation apertures allow air to pass therethrough towards the tail of the animal (not shown).

The padding insert 37 may be provided with a plurality of ribs (not shown) on the rear surface thereof to space the main body of the padding insert apart from the birthing sensor. Alternatively, the body and/or the strap of the birthing sensor may be provided with appropriate ribs or spacers thereon to keep the main body of the padding insert apart from the remainder of the birthing sensor. In this way, air will be able to pass between the birthing sensor and the padding insert and thereafter travel through the ventilation apertures towards the animal's tail.

Figure 12:
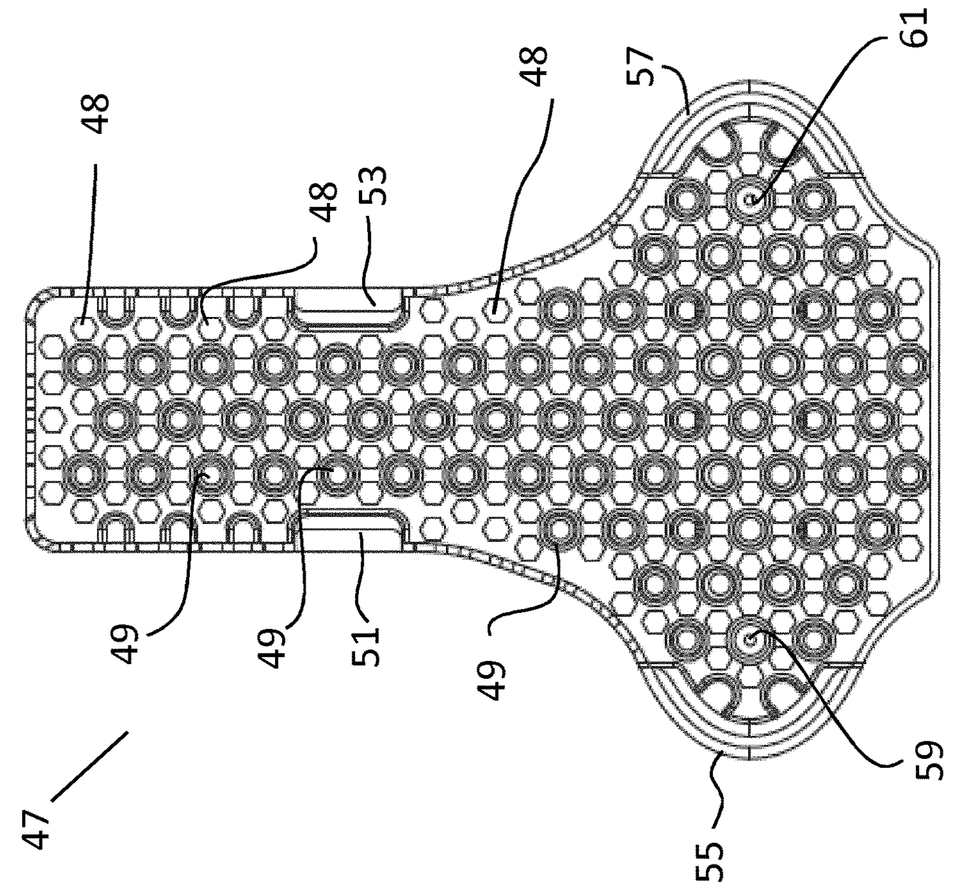
FIG. 12 is a rear view of a further alternative padding insert according to the invention.

Referring now to FIG. 12, there is shown a rear view of a further alternative embodiment of a padding insert 47 having a plurality of ventilation apertures 48 extending therethrough and a plurality of upstanding bosses 49 thereon. The padding insert further comprises a pair of inner wings 51, 53, a pair of outer wings 55, 57 and a pair of spigot-receiving apertures 59, 61. The inner wings 51, 53 are operable to engage a strap (not shown) and the outer wings 55, 57 are operable to engage the casing to maintain the padding insert 47 in position on the birthing sensor.

If desired, the inner wings 51, 53 and the outer wings 55, 57 could be omitted and the padding insert may be held in position by other means, for example spigots (not shown) in the spigot-receiving apertures 59, 61. Similarly, the spigots and spigot receiving apertures 59, 61 could be omitted in favour of the inner wings 51, 53 and the outer wings 55, 57. Further still, the padding insert may be held in position by other alternative attachment means.

The embodiment of padding insert 47 shown in FIG. 12 is seen as a particularly preferred embodiment of the padding insert according to the invention. The upstanding bosses 49 are directed towards the body of the casing and will keep the main body of the padding insert 47 spaced apart from the birthing sensor's casing and strap (not shown). Furthermore, the upstanding bosses 49 are spaced apart so that an air passageway will be provided between adjacent bosses. This will allow air to travel under the casing, through the air passageways between the bosses 49 and through the ventilation apertures 48 towards the animal's tail.

Figure 13:
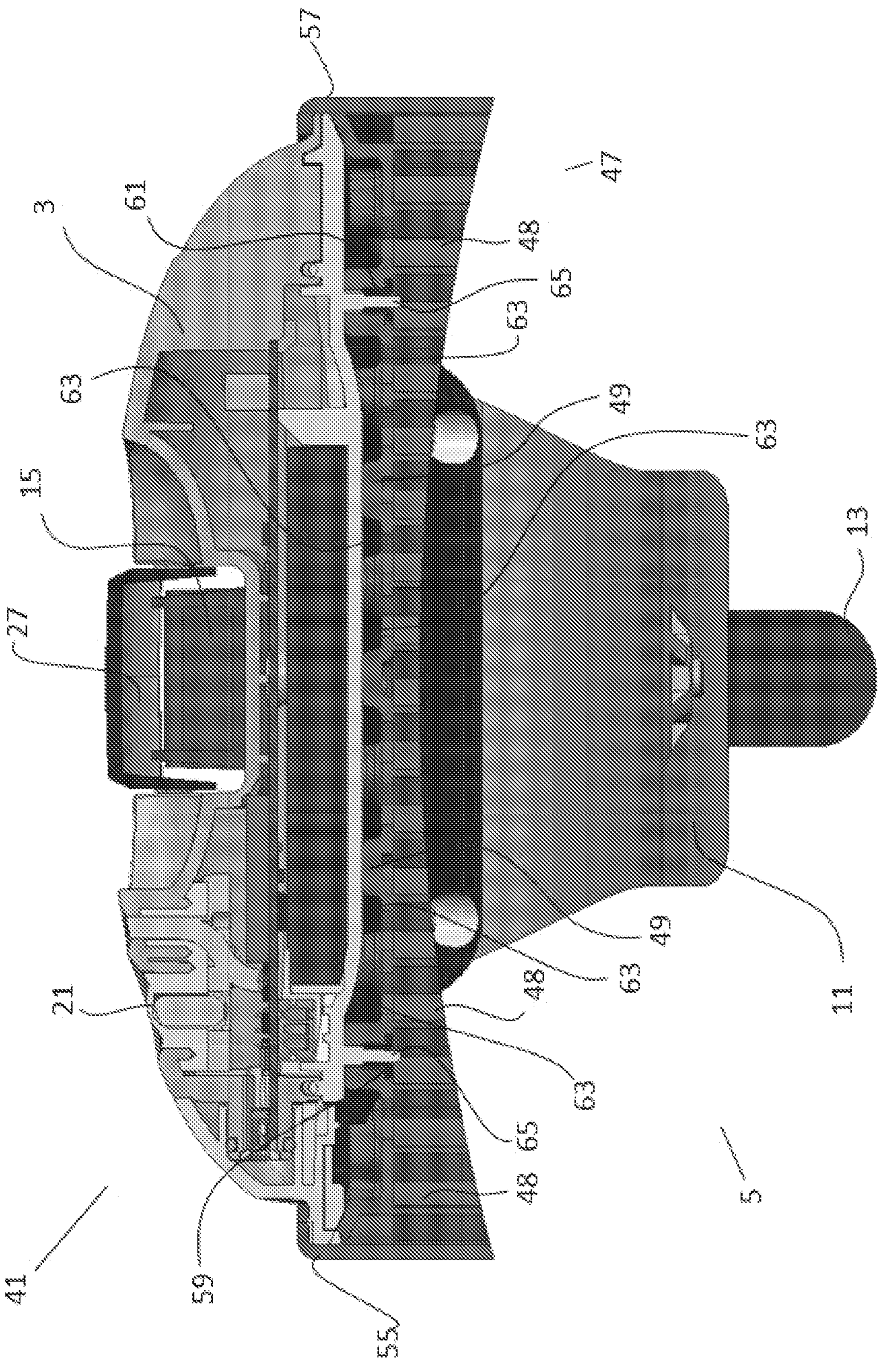
FIG. 13 is a cross section of an alternative embodiment of a birthing sensor.

Referring now to FIG. 13, there is shown a cross section of an alternative embodiment of the birthing sensor 41. This embodiment differs from the previous embodiment in that the birthing sensor 41 is equipped with the padding insert 47 as illustrated in FIG. 12. It can be seen that the ventilation apertures 48 extend through the padding insert 47. Furthermore, the upstanding bosses 49 contact the casing 3 and strap 5 and create air passageways 63 for air circulation between the casing and the padding insert and between the strap and the padding insert. Air passing through the air passageways is then able to travel through the ventilation apertures to the animal's tail. This greatly increases the comfort of the animal and obviates the development of sores on the animal's tail.

The outer wings 55, 57 engage the bottom and the top respectively of the casing 3. The outer wings 55, 57 extend around the bottom and top surfaces of the casing so that the padding insert is stretched across the casing 3. In this way, the elasticity of the resiliently deformable padding insert 47 will hold the padding insert in position on the casing 3.

Furthermore, a pair of spigots 65 are provided to engage the spigot-receiving apertures 59, 61 to further secure the padding insert in position. If desired, the wings 55, 57 and/or the spigots 65 could be omitted and alternative attachment means could be provided to hold the padding insert in position.

Figure 14:
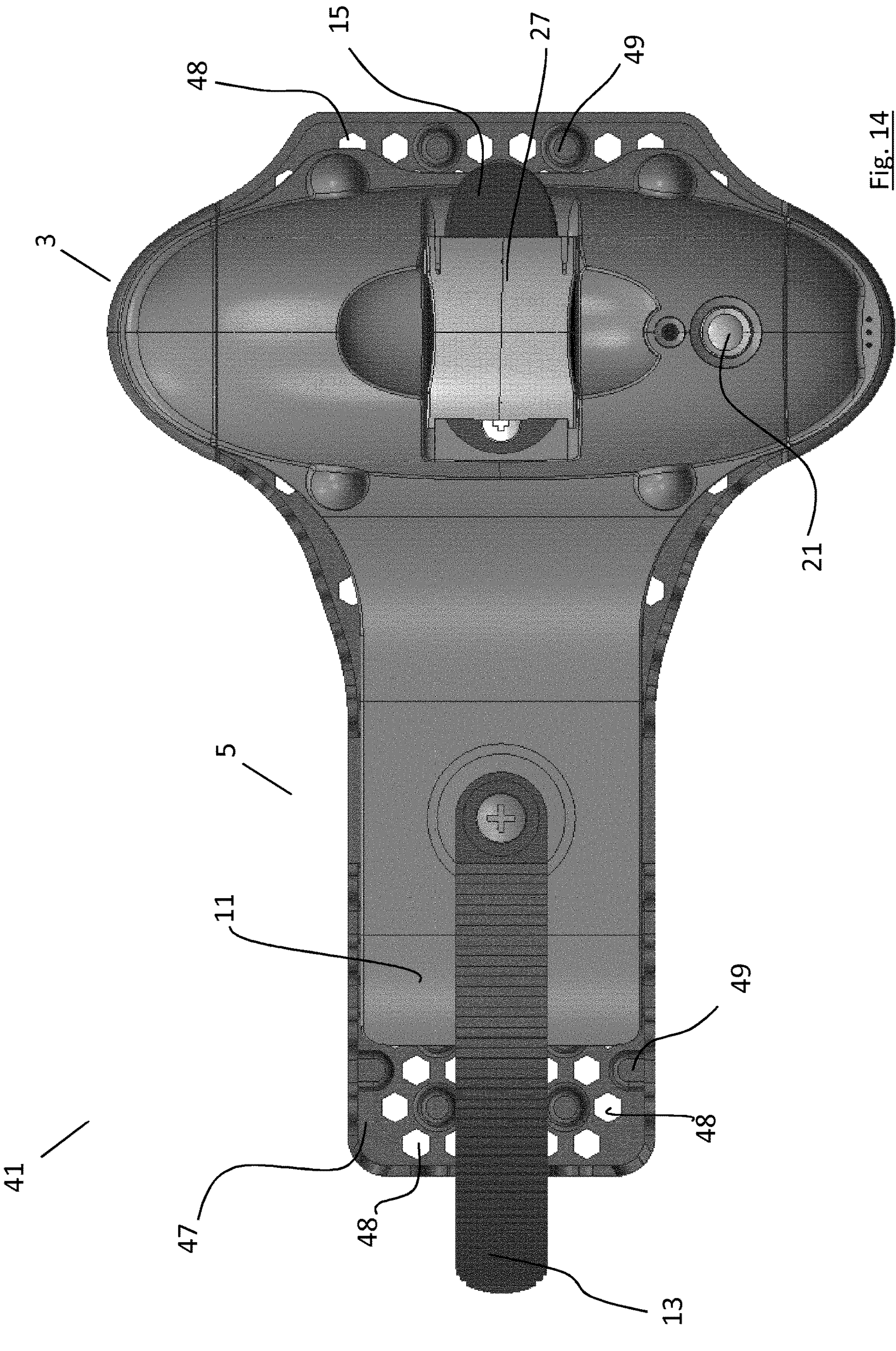
FIG. 14 is a front view of the alternative embodiment of the birthing sensor of FIG. 13.

Referring now to FIG. 14, there is shown a front view of the birthing sensor shown in FIG. 13. It can be seen that the upstanding bosses 49 extend from the padding insert 47 towards the casing 3 and strap 5. It can also be seen that the holes 48 extend through the padding insert 47.

In this specification the terms "comprise, comprises, comprised and comprising" and the terms "include, includes, included and including" are all deemed interchangeable and should be afforded the widest possible interpretation.

The invention is in no way limited to the embodiments hereinbefore described but may be varied in both construction and detail within the scope of the appended claims.

The invention claimed is:

1. A birthing sensor for mounting on a tail of a pregnant animal comprising a casing and an adjustable strap for securing the casing to the tail of the pregnant animal, the casing housing a PCB assembly having monitoring equipment, communication equipment and a power supply therein, and in which there is provided a padding insert mounted on the casing and the strap for location intermediate the casing, the strap and the animal's tail, the padding insert comprising a resiliently deformable material having a plurality of ventilation passageways formed therein for through passage of air when the birthing sensor is mounted on the tail of the pregnant animal, the padding insert further comprising a pair of inner wings and a pair of outer wings, the pair of outer wings being operable to engage the casing to maintain the padding insert in position on the birthing sensor, one of the pair of outer wings extending around a bottom surface of the casing and the other of the pair of outer wings extending around a top surface of the casing so that the padding insert is stretched across the casing and so that the elasticity of the resiliently deformable material will hold the padding insert in position on the casing, the pair of inner wings being operable to engage the strap.

2. The birthing sensor as claimed in claim 1 in which the padding insert comprises a plurality of ventilation apertures extending therethrough.

3. The birthing sensor as claimed in claim 1 in which the padding insert comprises a first sheet of the resiliently deformable material having a plurality of upstanding bosses formed on one surface thereof.

4. The birthing sensor as claimed in claim 3 in which the plurality of upstanding bosses are frustoconical in shape.

5. The birthing sensor as claimed in claim 3 in which there is provided a second sheet of the resiliently deformable material having a plurality of upstanding bosses formed on one surface thereof for placement overlapping the first sheet of the resiliently deformable material.

6. The birthing sensor as claimed in claim 5 in which the plurality of upstanding bosses formed on the second sheet of the resiliently deformable material are conical in shape.

7. The birthing sensor as claimed in claim 1 in which the padding insert is releasably secured to at least one of the casing and the strap.

8. The birthing sensor as claimed in claim 7 in which the casing is provided with at least one locating spigot and the padding insert is provided with at least one complementary spigot-receiving cutout.

9. The birthing sensor as claimed in claim 1 in which the padding insert is substantially T-shaped with the cross portion of the T-shaped padding insert aligned along the casing and the upright portion of the T-shaped padding insert aligned along the adjustable strap.

10. The birthing sensor as claimed in claim 1 in which the adjustable strap comprises a ratchet strap system including a toothed strap connected to the casing at one of its ends and a buckle mounted on the casing for releasably engaging the toothed strap intermediate its ends, the buckle being arranged so that as the buckle closes, the buckle tightens the strap by engaging one or more of the teeth on the strap and pulls the strap tighter.

11. The birthing sensor as claimed in claim 10 in which the buckle is inset into the casing.

12. The birthing sensor as claimed in claim 10 in which there is provided a removable protective cap mounted on the casing above the buckle.

13. The birthing sensor as claimed in claim 1 in which the adjustable strap is a two part strap including a first part formed integrally with the casing and extending outwardly therefrom and a second part connected to the first part, the second part being narrower than the first part and suitable for engagement in a buckle.

14. The birthing sensor as claimed in claim 1 in which the casing is turtle-shell shaped with a curved outer surface that tapers inwardly at each end.

15. The birthing sensor as claimed in claim 14 in which the power supply comprises a rechargeable battery and there is provided a battery charging port located at the end of the casing that in use is directed towards the ground and in which there is provided a removable gasket mounted over the battery charging port.

16. The birthing sensor as claimed in claim 1 in which the casing is constructed from a flexible plastic material.

17. The birthing sensor as claimed in claim 16 in which the casing is constructed from polypropylene.

18. The birthing sensor as claimed in claim 1 in which the padding insert is constructed from rubber silicone.

19. The birthing sensor as claimed in claim 1 in which the padding insert is constructed from latex rubber.

* * * * *